(12) United States Patent
Baseeth

(10) Patent No.: US 9,889,417 B2
(45) Date of Patent: Feb. 13, 2018

(54) EMULSIFIER FOR SOLUBILIZING POLAR SOLVENTS IN OILS AND POLYOLS

(71) Applicant: ARCHER DANIELS MIDLAND COMPANY, Decatur, IL (US)

(72) Inventor: Shireen Baseeth, Decatur, IL (US)

(73) Assignee: Archer Daniels Midland Company, Decatur, IL (US)

(*) Notice: Subject to any disclaimer, the term of this patent is extended or adjusted under 35 U.S.C. 154(b) by 452 days.

(21) Appl. No.: 14/400,715

(22) PCT Filed: May 15, 2013

(86) PCT No.: PCT/US2013/041125
§ 371 (c)(1),
(2) Date: Nov. 12, 2014

(87) PCT Pub. No.: WO2013/173447
PCT Pub. Date: Nov. 21, 2013

(65) Prior Publication Data
US 2015/0126624 A1    May 7, 2015

Related U.S. Application Data

(60) Provisional application No. 61/647,830, filed on May 16, 2012.

(51) Int. Cl.
| | | |
|---|---|---|
| B01F 17/14 | (2006.01) |
| B01F 17/34 | (2006.01) |
| B01F 17/00 | (2006.01) |
| A61K 8/39 | (2006.01) |
| A61K 8/49 | (2006.01) |
| A61K 8/55 | (2006.01) |
| A61Q 19/00 | (2006.01) |
| A61K 8/86 | (2006.01) |
| D06M 13/453 | (2006.01) |
| A23L 29/10 | (2016.01) |
| C09D 5/02 | (2006.01) |

(52) U.S. Cl.
CPC .......... *B01F 17/0092* (2013.01); *A23L 29/10* (2016.08); *A61K 8/39* (2013.01); *A61K 8/4973* (2013.01); *A61K 8/4993* (2013.01); *A61K 8/553* (2013.01); *A61K 8/86* (2013.01); *A61Q 19/00* (2013.01); *D06M 13/453* (2013.01); *A23V 2002/00* (2013.01); *A61K 2800/10* (2013.01); *C09D 5/02* (2013.01); *C09D 5/027* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,212,369 A * | 8/1940 | Jaeger | D06M 7/00 252/8.86 |
| 2,914,495 A * | 11/1959 | Gordon | C09D 131/04 106/14.13 |
| 6,117,434 A * | 9/2000 | Oyama | A61Q 19/00 424/401 |
| 9,315,652 B2 * | 4/2016 | Baseeth | C08K 5/521 |
| 2003/0059447 A1 * | 3/2003 | Lambers | A61K 8/41 424/401 |
| 2006/0153792 A1 * | 7/2006 | Arnaud | A61K 8/042 424/70.16 |
| 2006/0177409 A1 * | 8/2006 | Arnaud | A61K 8/97 424/74 |
| 2006/0286133 A1 * | 12/2006 | Fujino | A61K 8/06 424/401 |
| 2011/0250299 A1 * | 10/2011 | Baseeth | A23D 7/011 424/729 |
| 2014/0066347 A1 * | 3/2014 | Baseeth | A61Q 1/02 508/428 |
| 2014/0154357 A1 * | 6/2014 | Baseeth | A23J 7/00 426/62 |
| 2016/0324178 A1 * | 11/2016 | Stensrud | A23L 29/20 |

FOREIGN PATENT DOCUMENTS

| EP | 0 863 192 A1 * | 9/1998 | |
| WO | WO 2010/057007 A1 * | 5/2010 | |
| WO | WO 2010056833 A1 * | 5/2010 | ..... B01F 17/0085 |

OTHER PUBLICATIONS

Hawley's Condensed Chemical Dictionary, (2007), John Wiley & Sons, Inc., 32, 75, 467, 611-612, 664, 666, 669, 761, 772, 905, 1000-1001, 1005, 1016, 1050, 1164-1166, 1197,Online @ http://onlinelibrary.wiley.com/book/10.1002/9780470114735/titles, downloaded Mar. 13, 2017), pp. 1-7.*

"Polyurethanes", Ullmann's Encyclopedia of Industrial Chemistry, Norbert Adam et al., Published Online @ http://onlinelibrary.wiley.com/doi/10.1002/14356007.a21_665.pub2/abstract, on Jan. 15, 2005, pp. 545-559 & 600-604.*

* cited by examiner

*Primary Examiner* — Daniel S Metzmaier
(74) *Attorney, Agent, or Firm* — Andrew F. Nilles

(57) ABSTRACT

The present disclosure is directed to compositions having lecithin, a plasticizer, and an emulsifier. The composition may be used solubilize polar solvents in non-polar liquids. Methods of producing and using the compositions disclosed herein are also disclosed.

3 Claims, No Drawings

EMULSIFIER FOR SOLUBILIZING POLAR SOLVENTS IN OILS AND POLYOLS

CROSS-REFERENCE TO RELATED APPLICATIONS

This application is a national stage entry of International Application No. PCT/US13/41125, filed May 15, 2013, which itself claims priority to U.S. Provisional Patent Application No. 61/647,830, filed May 16, 2012, each of the contents of the entirety of which are incorporated by this reference.

TECHNICAL FIELD

The present disclosure is directed to emulsifiers comprising lecithin. The present disclosure is also directed to methods for the preparation and use of such emulsifiers.

BACKGROUND

The physical properties of polyurethane foams can vary based on variations in the components used to create the foams such as which crosslinker, catalyst, and blowing agent are used, as well as the concentrations of polyols, water, humectants, and surfactants are used in producing the foams. The type of surfactant can have an effect on the physical properties such as rigidity, density, and porosity of the foam and depends on factors such as: the emulsification property and its effect on the polyols, water, and humectants; the nucleation of the air bubbles; the stabilization of gas bubbles in the foam that don't coalesce; and the controlled cell opening. A single surfactant is rarely able to produce a foam with the desired physical properties, thus, typically a combination of surfactants are used. Traditionally, silicone surfactants have been used.

Surfactants with higher silicone contents lower the surface tension of the foams and, thus, help increase the amount of air bubbles in the foam during mixing. The foam formation includes various stages: generation of bubbles; packing of the foam network and stabilization; and final curing. In each of these stages, silicone surfactants are essential for the production of flexible, polyurethane foam systems. Without the use of a surfactant with such functionalities, the foaming system will experience major coalescence and collapse. Also, the size of cells in the foam and the air permeability of the foam is directly related to the functionality of the surfactant. Thus, surfactants having the proper functionality are requires in order to have the proper porosity, cell size, and density of the foams produced.

Recent trends have favored the use of natural oil polyols over their petroleum counterparts in the polyurethane market. However, the use of such natural oil polyols in place of their petroleum counterparts affects the resin stability of the foam which is a result of the nature of the different oil polyols being used. For instance, although soy polyols have good polarity resulting from the presence of hydroxyl groups in the molecule having a hydrophobic backbone, such properties are distinct from a petroleum polyol that is relatively non-polar and oleophilic. The difference in the polarity requires the use of a good surfactant with the soy polyols in order to keep crosslinkers such as water, glycerol, and their blends in homogenous foam in the polyol mixture to produce foam with the desired properties.

Lecithin has been used in foams as disclosed in US Patent Application US20110062370. Lecithin is a complex mixture of phospholipids and other components such as glycerol lipids. The use of standard fluid lecithin typically requires an aliphatic solvent to remain in solution. Without the use of such solvent, lecithin is typically modified or combined with other surfactants in order to improve functionality.

Polyols are integrally used in the rigid polyurethane industry. There is a growing desire to use more green or environmentally friendly products in such industry. One solution is to replace petroleum based polyols with soy based polyols. However, the replacement of petroleum based polyols with soy based polyols is problematic since polyurethane foams made with 100% soy polyol do not offer very good foam structure and rigidity due to the limited hydroxyl functionality of the soy polyols. Also, the different nature of the hydrocarbon groups in the petroleum based polyols v. the biobased polyols results in compatibility issues that need to be overcome. The addition of polar components such as glycols or glycerols to such soy polyols has shown some advantage in the resultant blends and the final properties of foams including such components depends on the types of polyol and its hydroxyl value, surfactant type and concentration, and blowing agent used. The compatibility of all of these components is a hurdle to the foam industry since it is important to get good compatibility without causing any phase separation for periods of time in order to achieve the desired physical properties.

Thus, the choice of which surfactant to use will depend on the chemical composition and processing of the polyols and other additives used to produce the foam. This diversity of foams being produced requires the use of surfactants that are not commonly used. Although short term stability can be achieved with different surfactants and their blends, getting long term stability is required to produce foam with reasonable consistency and superior functionalities. Thus, a need exists for an emulsifier system that can produce foams including natural oil polyols.

Lecithin is a polar lipid substance found in animal and plant tissues such as, for example, egg yolk and soy bean. Lecithin is composed of various constituents including, but not limited to, phospholipids, such as, for example, phosphatidyl choline ("PC"), phosphatidyl inositol ("PI"), and phosphatidyl ethanolamine ("PE"). With their unique surface active properties, lecithins can be used in a wide range of applications such as food, feed, pharmaceuticals, and a variety of industrial applications.

Further, lecithin may be used in applications where modification of the boundary layer between substances is desirable. In the presence of immiscible liquid phases, lecithin can reduce the interfacial surface tension and function as an emulsifier. When used with two or more solid phases, lecithin can function as a lubricant and/or release agent.

SUMMARY

In each of its various embodiments, the present invention fulfills these needs and discloses emulsifier systems that can be used for solubilizing polar solvents in oils and polyols. In other embodiments, the successful productions of foams including natural oil polyols using the emulsifier systems of the present invention are disclosed.

In one embodiment, a composition comprises lecithin, a plasticizer, and an emulsifier.

In another embodiment, uses of the composition for solubilizing polar solvents in non-polar liquids are also disclosed.

In a further embodiment, a method of solubilizing a polar solvent in a non-polar liquid comprises mixing lecithin with a plasticizer and a co-surfactant, thus producing an emulsifier blend, and combining the polar solvent, the non-polar liquid, and the emulsifier blend such that the polar solvent solubilized in the non-polar liquid.

It should be understood that this disclosure is not limited to the embodiments disclosed in this Summary, and it is intended to cover modifications that are within the spirit and scope of the invention, as defined by the claims.

DETAILED DESCRIPTION

In the present application, including the claims, other than in the operating examples or where otherwise indicated, all numbers expressing quantities or characteristics are to be understood as being modified in all instances by the term "about". Accordingly, unless indicated to the contrary, any numerical parameters set forth in the following description may vary depending on the desired properties one seeks to obtain in the compositions and methods according to the present disclosure. At the very least, and not as an attempt to limit the application of the doctrine of equivalents to the scope of the claims, each numerical parameter described in the present description should at least be construed in light of the number of reported significant digits and by applying ordinary rounding techniques.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as set forth herein supersedes any conflicting material incorporated herein by reference. Any material, or portion thereof, that is said to be incorporated by reference herein, but which conflicts with existing definitions, statements, or other disclosure material set forth herein is only incorporated to the extent that no conflict arises between that incorporated material and the existing disclosure material.

The embodiments disclosed herein are directed to compositions and methods that comprise lecithin. In various embodiments, the composition is a blend of lecithin in amounts ranging from 5% to 95% by weight of the disclosed compositions, and in certain embodiments from 70% to 95%; and the plasticizer in amounts ranging from 5% to 95% by weight of the disclosed compositions, and in certain embodiments from 5% to 30%.

It has been found that the combination of lecithin and one or more plasticizers results in a composition that is able to solubilize a polar solvent in an oil or polyol.

Lecithins suitable for use in the disclosed compositions and methods include, but are not limited to, crude filtered lecithin, fluid lecithin, de-oiled lecithin, chemically and/or enzymatically modified lecithin, standardized lecithin, and blends of any thereof. Lecithins employed in the present disclosure generally tend to have a hydrophilic-lipophilic balance ("HLB") value ranging from 1.0 to 10.0 depending on the processing conditions and additives used to obtain the lecithin and produce the lecithin product. For example, crude filtered lecithin has an HLB value of approximately 4.0 and favors the formation of water-in-oil emulsions. Standardized lecithin includes co-emulsifiers having HLB values ranging from 10.0 to 24.0, which results in lecithin compositions having HLB values of 7.0 to 12.0 and favoring oil-in-water emulsions. Any lecithin or combinations of lecithins are suitable for use in the disclosed compositions and methods regardless of the initial HLB value of the lecithin. Lecithins useful in the disclosed compositions and methods may comprise co-emulsifiers having a hydrophilic-lipophilic balance value ranging from 10.0 to 24.0, and in certain embodiments 10.0 to 18.0.

The emulsifier and/or surfactant properties of an amphiphilic substance such as lecithin, for example, may be predicted at least in part by the hydrophilic-lipophilic balance ("HLB") value of the substance. The HLB value may function as an index of the relative preference of an amphiphilic substance for oil or water—the higher the HLB value, the more hydrophilic the molecule; the lower the HLB value, the more hydrophobic the molecule. A description of HLB values is provided in U.S. Pat. No. 6,677,327, which is incorporated by reference herein in its entirety. HLB is also described in Griffin, "Classification of Surface-Active Agents by 'HLB,'" *J. Soc. Cosmetic Chemists* 1 (1949); Griffin, "Calculation of HLB Values of Non-Ionic Surfactants," *J. Soc. Cosmetic Chemists* 5 (1954); Davies, "A quantitative kinetic theory of emulsion type, I. Physical chemistry of the emulsifying agent," *Gas/Liquid and Liquid/Liquid Interfaces, Proceedings of the 2d International Congress on Surface Activity* (1957); and Schick, "Nonionic Surfactants: Physical Chemistry", Marcel Dekker, Inc., New York, N.Y., pp. 439-47 (1987), each of which is incorporated by reference herein in its entirety.

In one embodiment, the nonionic co-surfactant is selected from the group consisting of ethoxylated monoglycerides, fatty acid ethoxylates, polyoxyethylene alkyl ethers, polyoxyethylene alkyl esters, propylene glycol alkyl esters, polyglycerol esters, glycols, polyoxyethylene sorbitan alkyls esters, mono and di esters of polyols, derivatives of any thereof, and combinations of any thereof.

In various embodiments, the plasticizer used in the disclosed compositions and methods may be selected from the group consisting of a lactate, a citrate, an adipate, an ester of a lactate, an ester of a citrate, an ester of an adipate, a pentaerythritol ester, an isosorbide ester, and combinations of any thereof. The plasticizer may also be a bio-derived plasticizer. Substances of a bio-derived origin are derived from biological materials as opposed to being derived from petrochemical sources. Bio-derived substances may be differentiated from petroleum derived substances by their carbon isotope ratios using ASTM International Radioisotope Standard Method D 6866. As used herein, the term "bio-derived" refers to being derived from or synthesized by a renewable biological feedstock, such as, for example, an agricultural, forestry, plant, fungal, bacterial, or animal feedstock.

Various agencies have established certification requirements for determining bio-derived content. These methods require the measurement of variations in isotopic abundance between bio-derived products and petroleum derived products, for example, by liquid scintillation counting, accelerator mass spectrometry, or high precision isotope ratio mass spectrometry. Isotopic ratios of the isotopes of carbon, such as the $^{13}C/^{12}C$ carbon isotopic ratio or the $^{14}C/^{12}C$ carbon isotopic ratio, can be determined using isotope ratio mass spectrometry with a high degree of precision. Studies have shown that isotopic fractionation due to physiological processes, such as, for example, $CO_2$ transport within plants during photosynthesis, leads to specific isotopic ratios in natural or bio-derived compounds. Petroleum and petroleum derived products have a different $^{13}C/^{12}C$ carbon isotopic ratio due to different chemical processes and isotopic fractionation during the generation of petroleum. In addition, radioactive decay of the unstable $^{14}C$ carbon radioisotope leads to different isotope ratios in bio-derived products compared to petroleum products. Bio-derived content of a product may be verified by ASTM International Radioisotope Standard Method D 6866. ASTM International Radioisotope Standard Method D 6866 determines bio-derived content of a material based on the amount of bio-derived carbon in the material or product as a percent of the weight (mass) of the total organic carbon in the material or product. Bio-derived products will have a carbon isotope ratio characteristic of a biologically derived composition.

Bio-derived materials offer an attractive alternative for industrial manufacturers looking to reduce or replace their reliance on petrochemicals and petroleum derived products. The replacement of petrochemicals and petroleum derived products with products and/or feed stocks derived from biological sources (i.e., bio-based products) offer many advantages. For example, products and feed stocks from biological sources are typically a renewable resource. In most instances, bio-derived chemicals and products formed therefrom are less burdensome on the environment than petrochemicals and products formed from petrochemicals. As the supply of easily extracted petrochemicals continues to be depleted, the economics of petrochemical production will likely force the cost of the petrochemicals and petroleum derived products to higher prices compared to bio-based products. In addition, companies may benefit from the marketing advantages associated with bio-derived products from renewable resources in the view of a public becoming more concerned with the supply of petrochemicals.

In various embodiments, plasticizers suitable for use in the disclosed compositions and methods include, but are not limited to propylene glycol monoester (PGME), butyl benzyl phthalate (BBP), di-n-butyl maleate (DBM), di-n-butyl phthalate (DBP), diethylene glycol dibenzoate (DEGD), di(2-ethylhexyl) phthalate (DEHP), dioctyl phthalate (DOP), diethyl phthalate (DEP), diisobutyl phthalate (DIBP), diisodecyl adipate (DIDA), diisodecyl phthalate (DIDP), diisoheptyl phthalate (DIHP), diisononyl adipate (DINA), diisononyl cyclohexane-1,2-dicarboxylate (DINCH), diisononyl phthalate (DINP), diisooctyl adipate (DIOA), diisooctyl phthalate (DIOP), dimenthyl phthalate (DMP), di-n-hexyl phthalate (DnHP), di-n-octyl adipate (DnOA), di-n-octyl phthalate (DnOP), dinonyl phthalate (DNP), dioctyl adipate (DOA), di-(2-ethylhexyl) adipate (DEHA), dioctyl maleate (DOM), dioctyl sebacate (DOS), dioctyl terephalate (DOTP), dioctyl azelate (DOZ), dipropylene glycol dibenzoate (DPGB), di(2-propylheptyl) phthalate (DPHP), ditridecyl adipate (DTDA), ditridecyl phthalate (DTDP), diundecyl phthalate (DUP), 2-ethylhexanol (2-EH), epoxidized linseed oil (ELO), epoxidized soybean oil (ESO), general-purpose phthalate (GPP), isodecyl alcohol (IDA), isononyl alcohol (INA), phthalic anhydride (PA), 2-propylheptanol (2-PH), polyvinyl chloride (PVC), tricresyl phosphate (TCP), triisononyl trimellitate (TINTM), triiisooctyl trimellitate (TIOTM), trimellitic anhydride (TMA), trioctyl trimellitate (TOTM), triphenyl phosphate (TPP), trixylyl phosphate (TXP), undecyl dodecyl phthalate (UDP), soybean oil, medium chain triglycerides, a polyglycerol ester, epoxidised methyl soyate, a monoester of a polyol, a diester of a polyol, hydroxymethyl furfural, isosorbide, and combinations of any thereof.

As used herein, the term "DEHA" includes di-(2-ethylhexyl) adipate. DEHA is also referred to as dioctyl adipate or "DOA" in the art. As used herein, unless otherwise indicated, dioctyl adipate ("DOA") refers to the ester of adipic acid and linear n-octanol.

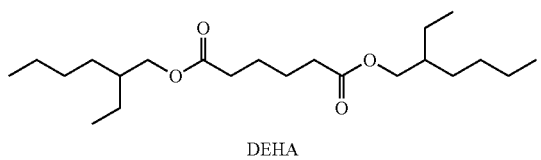 [SMILES: CCCCC(CC)COC(=O)CCCCC(=O)OCC(CC)CCCC]

DEHA

It is also important to note that both moieties may be used as plasticizers—alone, together, or in combination with other plasticizers—in various embodiments described herein.

In various embodiments, the disclosed compositions may also comprise one or more co-surfactants. The one or more co-surfactants may comprise one or more anionic surfactants, one or more non-ionic surfactants, or combinations of one or more anionic surfactants and one or more non-ionic surfactants. In various embodiments, the co-surfactant or co-surfactant combinations may have a hydrophilic-lipophilic balance ranging from 10.0 to 24.0, and in some embodiments from 10.0 to 18.0. In various embodiments, the lecithin may comprise from 5% to 95% by weight of the disclosed composition, in some embodiments from 60% to 90%, and in other embodiments from 80% to 90%; the plasticizer may comprise from 1% to 20% by weight of the disclosed composition, in some embodiments from 5% to 15%, and in other embodiments from 5% to 10% or 10% to 15%; and the co-surfactant may comprise from 2% to 20% by weight of the composition, in some embodiments from 5% to 15%, and in other embodiments from 10% to 15%.

Anionic surfactants suitable for use in the disclosed compositions and methods include, but are not limited to, sodium and potassium salts of straight-chain fatty acids, polyoxyethylenated fatty alcohol carboxylates, linear alkyl benzene sulfonates, alpha olefin sulfonates, sulfonated fatty acid methyl ester, arylalkanesulfonates, sulfosuccinate esters, alkyldiphenylether(di)sulfonates, alkylnaphthalenesulfonates, isoethionates, alkylether sulfates, sulfonated oils, fatty acid monoethanolamide sulfates, polyoxyethylene fatty acid monoethanolamide sulfates, aliphatic phosphate esters, nonylphenolphosphate esters, sarcosinates, fluorinated anionics, anionic surfactants derived from oleochemicals, and combinations of any thereof. In various embodiments, the surfactant comprises an anionic surfactant, such as, for example, a phosphate ester.

Non-ionic surfactants suitable for use in the disclosed compositions and methods include, but are not limited to, sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl) ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil, sorbitol hexaesters, ethoxylated castor oil, ethoxylated soybean oil, rapeseed oil ethoxylate, ethoxylated fatty acids, ethoxylated fatty alcohols, ethoxylated polyoxyethylene sorbitol tetraoleate, glycerol and polyethylene glycol mixed esters, alcohols, polyglycerol esters, monoglycerides, sucrose esters, alkyl polyglycosides, polysorbates, fatty alkanolamides, polyglycol ethers, derivatives of any thereof, and combinations of any thereof.

In various embodiments, the surfactant comprises a non-ionic surfactant, such as, for example, ethoxylated monoglycerides, fatty acid ethoxylates, polyoxyethylene alkyl ethers, polyoxyethylene alkyl esters, sorbitan alkyl esters, propylene glycol esters, glycol esters, polyoxyethylene sorbitan alkyls esters, glycerol esters, derivatives of any thereof, and combinations of any thereof.

In various embodiments, the disclosed compositions and methods may comprise lecithin, a plasticizer, a first non-ionic surfactant, and a second non-ionic surfactant that is different than the first non-ionic surfactant. In various embodiments, the plasticizer may comprise di-(2-ethylhexyl) adipate and one of the non-ionic surfactants may comprise a fatty acid ethoxylate. In various embodiments, the first non-ionic surfactant and the second non-ionic surfactant may be present in the disclosed composition in a weight ratio ranging from 1:9 to 9:1. The first and the second non-ionic surfactant may comprise 1% to 10% by weight of the disclosed composition, and in some embodiments from 3% to 7%.

In various embodiments, the disclosed compositions find utility in products selected from the group consisting of a paint, an ink, a coating, a magnetic fluid, concrete, a ceramic, a textile auxiliary agent, an aid in leather finishing, a plastic compounding agent, a lubricant, an oilfield drilling additive, a mold release agent, a cosmetic, and a composite used in engineered woods ("wood composite").

Water-based coatings may include, but are not limited to, latex paints. In various embodiments, the disclosed compositions may be used as dispersion vehicles for pigments in paint and ink formulations. In various embodiments, the disclosed compositions advantageously aid in pigment processing, including, but not limited to, grinding, milling and release aids, which may contribute to improved gloss, colorant and body in pigmented formulations. The low viscosity of the disclosed compositions provides improved coating uniformity to pigments and other particulates in dispersions. In this context, among others, the disclosed compositions provide improved dispersant, wetting agent, and/or stabilizer properties and performance.

In various other embodiments, the disclosed compositions may be used in magnetic fluid applications. In one embodiment, the disclosed compositions may be used to stabilize magnetic particles in a solvent base, including, but not limited to, a mixture of a base oil and an ester compound. The improved wetting and dispersant properties of the disclosed compositions result in reduced agglomeration of the suspended particles in magnetic fluids without resulting in adverse effects on the viscosity of the fluid.

The disclosed compositions may also be used in nanotechnology applications. In one embodiment, the disclosed compositions may be used as a dispersant, wetting agent, solubilizer, and/or stabilizer in nanoparticle suspensions. Additional applications for the disclosed compositions and methods include, but are not limited to, use in fiberglass, concrete, ceramics, plastics, and composites. Additional uses of the disclosed compositions include, but are not limited to, uses as textile auxiliary agents, leather finishing agents, plastic compounding agents, lubricants, oilfield drilling additives, emollients, film-formers, and mold release agents.

The embodiments disclosed herein are also directed to methods of preparing the disclosed compositions. In various embodiments, lecithin is heated to a temperature above ambient temperature, a plasticizer is added to the lecithin at the elevated temperature, and the plasticizer and lecithin are mixed together to form a lecithin-plasticizer blend. The blend is cooled to ambient temperature. The resulting blend has a viscosity lower than the lecithin ingredient alone, which may be less than 3000 cP. In various embodiments, the viscosity of the lecithin-plasticizer blend may be less than 2000 cP, less than 500 cP, or less than 100 cP. In various other embodiments, one or more non-ionic emulsifiers may be added to the lecithin either before or simultaneously with one or more plasticizers. The one or more non-ionic emulsifiers may alternatively be added to the blend of the lecithin and the one or more plasticizers.

The versatility of the surfactant package or system was determined by being able to solubilize 10% in soybean oil, tall fatty acids, and castor oil. Solubilization of polar components in non-polar oils typically requires very high surfactant concentrations that form a microemulsion. One characteristic of the surfactant packages disclosed herein is that polar additives are able to be solubilized in a variety of oils with a limited amount of the surfactant package.

EXAMPLES

The following exemplary, non-limiting examples are provided to further describe the embodiments presented herein. Those having ordinary skill in the art will appreciate that variation of these Examples are possible within the scope of the invention.

Example 1

A blend of crude filtered lecithin (Yelkin® T, Archer-Daniels-Midland Company, Decatur, Ill., USA), DEHA (Plastomoll® DOA, BASF, North Mount Olive, N.J., USA), a tall fatty acid ethoxylate surfactant (Ninex® MT-610, Stepan Company, Northfield, Ill., USA), and a phosphate ester surfactant (Stepfac™ 8170, Stepan Company, Northfield, Ill., USA) was prepared. The blend was 80% lecithin, 10% DEHA, 7% fatty acid ethoxylate surfactant, and 3% phosphate ester surfactant by weight. The blend was prepared by mixing the lecithin, DEHA, and two surfactants and heating the mixture to 50° C. under constant stirring for 30 to 60 minutes. The blend was cooled to ambient temperature (approximately 25° C.). The blend was a free-flowing liquid at ambient temperature. The blend was water dispersible.

Example 2

A blend of crude filtered lecithin (Yelkin® T, Archer-Daniels-Midland Company, Decatur, Ill., USA), DEHA (Plastomoll® DOA, BASF, North Mount Olive, N.J., USA), a tall fatty acid ethoxylate surfactant (Ninex® MT-610, Stepan Company, Northfield, Ill., USA), and a phosphate ester surfactant (Surfonic PE-BP 2, Huntsman, Woodland, Tex., USA) was prepared. The blend was 80% lecithin, 10% DEHA, 7% fatty acid ethoxylate surfactant, and 3% phosphate ester surfactant by weight. The blend was prepared by mixing the lecithin, DEHA, and two surfactants and heating the mixture to 50° C. under constant stirring for 30 to 60 minutes. The blend was cooled to ambient temperature (approximately 25° C.). The blend was a free-flowing liquid at ambient temperature. The blend was water dispersible.

Example 3

A lecithin based microemulsion was produced with the ingredients of Table 1.

TABLE 1

| Ingredient | Amount |
| --- | --- |
| YELKIN T | 36% |
| Polysorbate 80 | 10.4% |
| Fatty acids | 3.2% |
| 88% strength lactic acid | 8% |
| Sodium lactate | 18.4% |
| Ethyl lactate | 4.0% |
| Mineral oil | 20.0% |

To produce the microemulsion, a lecithin-cosurfactant blend was prepared by mixing: the YELKIN T brand lecithin (available from Archer-Daniels-Midland Company of, Decatur, Ill.); a co-surfactant, polysorbate 80 (available from BASF, New Jersey); and fatty acids. The components were mixed at 50° C. under constant stirring for between 30 minutes to 60 minutes, thus producing an amber, transparent lecithin concentrate. The lecithin-cosurfactant blend is miscible in mineral oil.

The lecithin-cosurfactant blend was mixed with the sodium lactate (available from Archer-Daniels-Midland Company, Decatur, Ill.), followed by the 88% strength lactic acid (available from Archer-Daniels-Midland Company, Decatur, Ill.). To this blend, the ethyl lactate (available from Archer-Daniels-Midland Company, Decatur, Ill.) was added. 80 g of this blend was mixed with 20 g mineral oil to form a microemulsion that was clear and transparent. This lecithin based microemulsion is infinitely miscible in mineral oil. In addition, this lecithin based microemulsion can solubilize additional water in an amount of up to 5-40% wt/wt and still maintain its clear and transparent microemulsion phase.

Example 4

A lecithin based microemulsion was produced with the ingredients of Table 2.

TABLE 2

| Ingredient | Amount |
| --- | --- |
| YELKIN T | 36% |
| Polysorbate 80 | 10.4% |
| Fatty acids | 3.2% |
| 88% strength lactic acid | 8% |
| Sodium lactate | 18.4% |
| Ethyl lactate | 24.0% |

To produce the microemulsion, a lecithin-cosurfactant blend was prepared by mixing: the YELKIN T brand lecithin (available from Archer-Daniels-Midland Company of, Decatur, Ill.); a co-surfactant, polysorbate 80 (available from BASF, New Jersey); and fatty acids. The components were mixed at 50° C. under constant stirring for between 30 minutes to 60 minutes, thus producing amber, transparent lecithin concentrate.

The lecithin-cosurfactant blend was mixed with the sodium lactate (available from Archer-Daniels-Midland Company, Decatur, Ill.), followed by the 88% strength lactic acid (available from Archer-Daniels-Midland Company, Decatur, Ill.). To this blend, the ethyl lactate (available from Archer-Daniels-Midland Company, Decatur, Ill.) was added. 90 g of this blend was mixed with 10 g glycerol to form a microemulsion that was clear and transparent. In addition, this lecithin based microemulsion can solubilize additional water in an amount of up to 5-40% wt/wt and still maintain its clear and transparent microemulsion phase.

Example 5

50% by weight of the composition produced in Example 1 was mixed with 50% by weight of ethoxylated monoglycerides (Mazol 80, available from BASF) to produce an emulsifier blend using propylene glycol as a co-solvent.

The ability of the emulsifier blend to stabilize of mixture of a biobased polyol (soy polyol) with a petroleum based polyol in the presence of glycerol was tested. The compounds used and percentages of each are set forth in Table 3. The compounds were weighed in a glass jar, mixed well with sweep agitation for 5 minutes at 60° C., and monitored for stability over time for any phase separation.

TABLE 3

| Sample | Soy polyol (%) | Petroleum polyol (%) | Glycerol (%) | Emulsifier blend (%) |
| --- | --- | --- | --- | --- |
| A | 63 | 35 | 2 | 4 |
| B | 61 | 35 | 4 | 4 |
| C | 59 | 35 | 6 | 4 |
| D | 57 | 35 | 8 | 4 |
| E | 55 | 35 | 10 | 4 |

A water soluble dye was added to the glycerol before blending in order to be able to visualize any phase separation in the blends of Table 3. This was helpful since the refractive index of glycerol and Pyrex glass are very similar (RI of about 1.47). The presence of the emulsifier blend helped reduce the amount of phase separation as compared to a control sample that did not have the emulsifier blend, where the glycerol with the water soluble dye settled at the bottom.

The present invention has been described with reference to certain exemplary and illustrative embodiments, compositions and uses thereof. However, it will be recognized by persons having ordinary skill in the art that various substitutions, modifications or combinations of any of the exemplary embodiments may be made without departing from the scope of the invention. Thus, the invention is not limited by the description of the exemplary and illustrative embodiments, but rather by the appended claims.

What is claimed is:

1. A method of solubilizing a polar solvent in a non-polar liquid, the method comprising:
   mixing lecithin with a plasticizer and a co-surfactant, thus producing an emulsifier blend; and
   mixing the non-polar liquid comprising a biobased polyol and a petroleum polyol with the emulsifier blend and the polar solvent, such that the emulsifier blend stabilizes the combination of the biobased polyol with the petroleum based polyol.

2. The method of claim 1, wherein the polar solvent is glycerol.

3. The method of claim 1, wherein the polar solvent is propylene glycol.

* * * * *